US008845585B2

(12) United States Patent
Wang et al.

(10) Patent No.: US 8,845,585 B2
(45) Date of Patent: Sep. 30, 2014

(54) INTRAVENOUS CATHETER SET

(71) Applicants: Chih-Ming Wang, Keelung (TW);
Wei-Ting Wang, Keelung (TW)

(72) Inventors: Chih-Ming Wang, Keelung (TW);
Wei-Ting Wang, Keelung (TW)

(*) Notice: Subject to any disclaimer, the term of this patent is extended or adjusted under 35 U.S.C. 154(b) by 32 days.

(21) Appl. No.: 13/748,634

(22) Filed: Jan. 24, 2013

(65) Prior Publication Data
US 2013/0211325 A1 Aug. 15, 2013

(30) Foreign Application Priority Data

Feb. 13, 2012 (TW) .............................. 101104601 A

(51) Int. Cl.
*A61M 5/00* (2006.01)
*A61M 5/32* (2006.01)

(52) U.S. Cl.
CPC .................. *A61M 5/3221* (2013.01)
USPC ....................................................... 604/110

(58) Field of Classification Search
CPC .. A61M 5/322; A61M 5/3129; A61M 5/3148
USPC ................................................ 604/187, 110
See application file for complete search history.

(56) References Cited

U.S. PATENT DOCUMENTS 5,195,985 A * 3/1993 Hall .............................. 604/195

OTHER PUBLICATIONS

MP4 video file, "Intravenous Catheter Set," 59 sec, 2.3 MB, undated.

* cited by examiner

*Primary Examiner* — Nicholas Lucchesi
*Assistant Examiner* — Melissa A Snyder

(57) ABSTRACT

The invention includes a barrel, a needle assembly, a catheter, a stopper and a vacuum generator. The needle assembly is disposed in the barrel and has a needle, a needle hub and a needle piston. The needle piston is fastened onto the needle hub. The catheter is axially connected onto the needle hub and passed through by the needle. The stopper is operably disposed at the first end of the barrel and normally stops the needle hub from moving. The vacuum generator has a plunger and a vacuum piston mounted on an end thereof. The vacuum piston is slidably received in the barrel and normally abuts against the needle piston, and the plunger protrudes from the second end of the barrel. The needle assembly will be pulled and retracted in the barrel when the plunger is pulled outward and the stopper releases the needle hub.

9 Claims, 8 Drawing Sheets

INTRAVENOUS CATHETER SET

BACKGROUND OF THE INVENTION

1. Technical Field

The invention relates to disposable hypodermics, particularly to safety catheters with retractable needles.

2. Related Art

A conventional intravenous catheter set is composed of a needle, a catheter and a needle cap. The catheter is passed through by the needle and the needle cap covers the needle and catheter. The user first uncovers the needle cap before inserting the tip of needle along with the catheter into a patient's skin. Then, the user extracted the needle by abutting the catheter against the patent's skin, leaving the catheter indwelled in place of the patient's skin. The needle is a disposable piece. A used needle is very dangerous and infectious and must be carefully cloaked by the cap. Although a kind of safety catheter containing a pre-established vacuum has appeared in the market, it needs to maintain the pre-established vacuum before the use, otherwise its safety mechanism will not be workable. Adversely, an unworkable safety catheter is more dangerous than an intravenous catheter without a safety mechanism because users are more likely to be injured if the safety catheter is not being workable.

SUMMARY OF THE INVENTION

An object of the invention is to provide an intravenous catheter set, which does not need to provide a pre-establish vacuum long before the use, and thus avoid a problem of maintaining the vacuum during a possible long period of time, such as storage or delivery, before the use. The invention provides users' safety by manually generating a vacuum immediately before the use.

To accomplish the above object, the intravenous catheter set of the invention includes a barrel, a needle assembly, a catheter, a stopper and a vacuum generator. The needle assembly is disposed in the barrel and has a needle, a needle hub and a needle piston. The needle piston is fastened onto the needle hub. The catheter is axially connected onto the needle hub and passed through by the needle. The stopper is operably disposed at the first end of the barrel and normally stops the needle hub from moving. The vacuum generator has a plunger and a vacuum piston mounted on an end thereof. The vacuum piston is slidably received in the barrel and normally abuts against the needle piston, and the plunger protrudes from the second end of the barrel. The needle assembly will be pulled and retracted in the barrel when the plunger is pulled outward and the stopper releases the needle hub.

DETAILED DESCRIPTION OF THE INVENTION

Figure 1A:
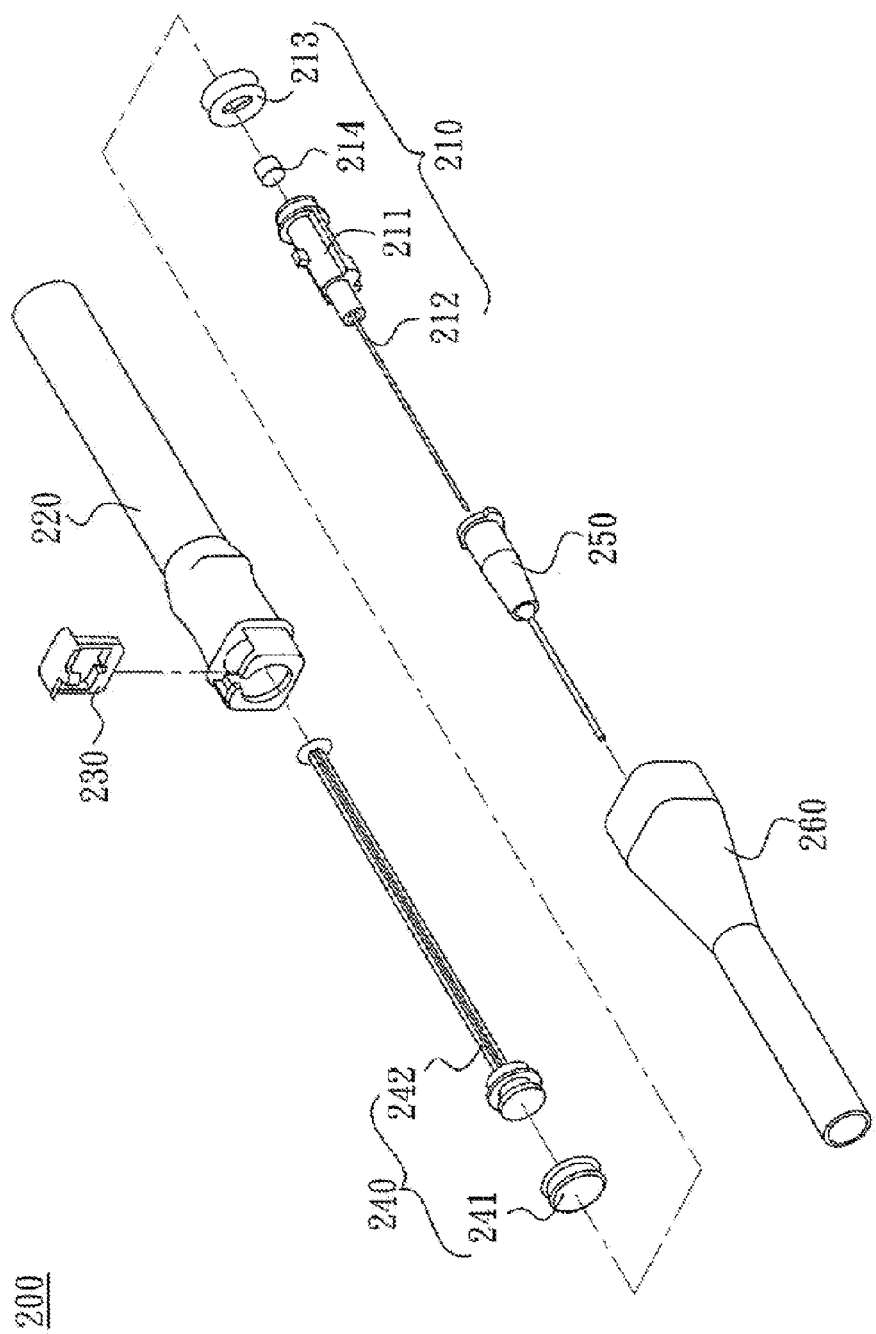
FIG. 1A is an exploded view of the invention.
Figure 1B:
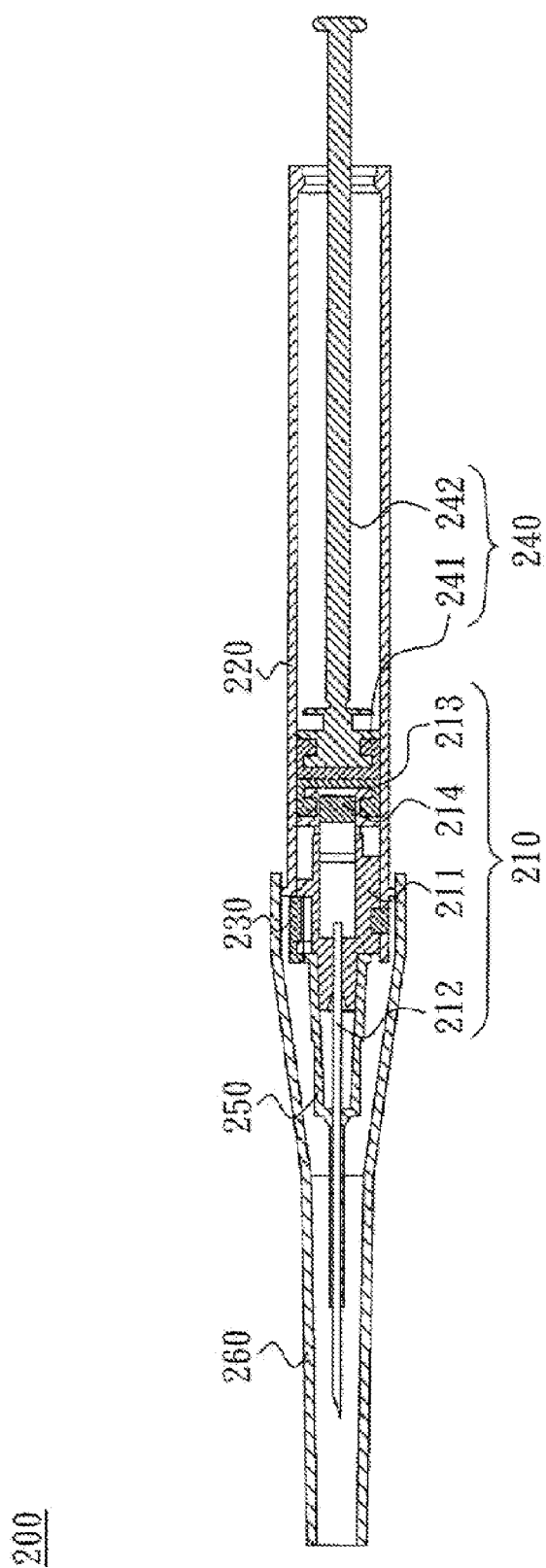
FIG. 1B is a longitudinal cross section view of the invention.

Please refer to FIGS. 1A and 1B. The intravenous catheter set 200 includes a barrel 220, a needle assembly 210, a catheter 250, a stopper 230 and a vacuum generator 240. The barrel 220 has a first end and a second end. The needle assembly 210 is disposed in the first end of the barrel 220. The stopper 230 is operably disposed in the first end of the barrel 220 for selectively and normally stopping the needle assembly 210 from moving. The vacuum generator 240 is operably disposed in the barrel 220 for manually making a vacuum therein. The catheter 250 is axially removably connected onto the needle assembly 210. Optionally, the invention further includes a cap 260 for protectively covering the needle assembly 210 and catheter 250.

Figure 1C:
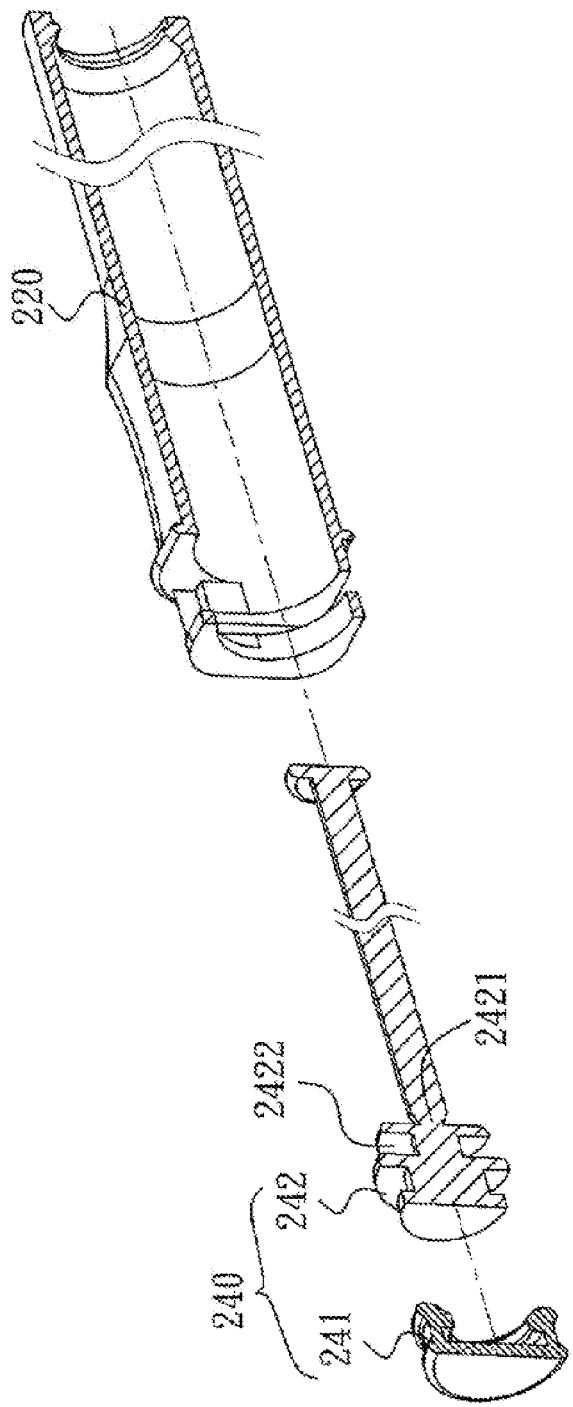
FIG. 1C is a partial enlarged view of the barrel and vacuum generator.
Figure 1D:
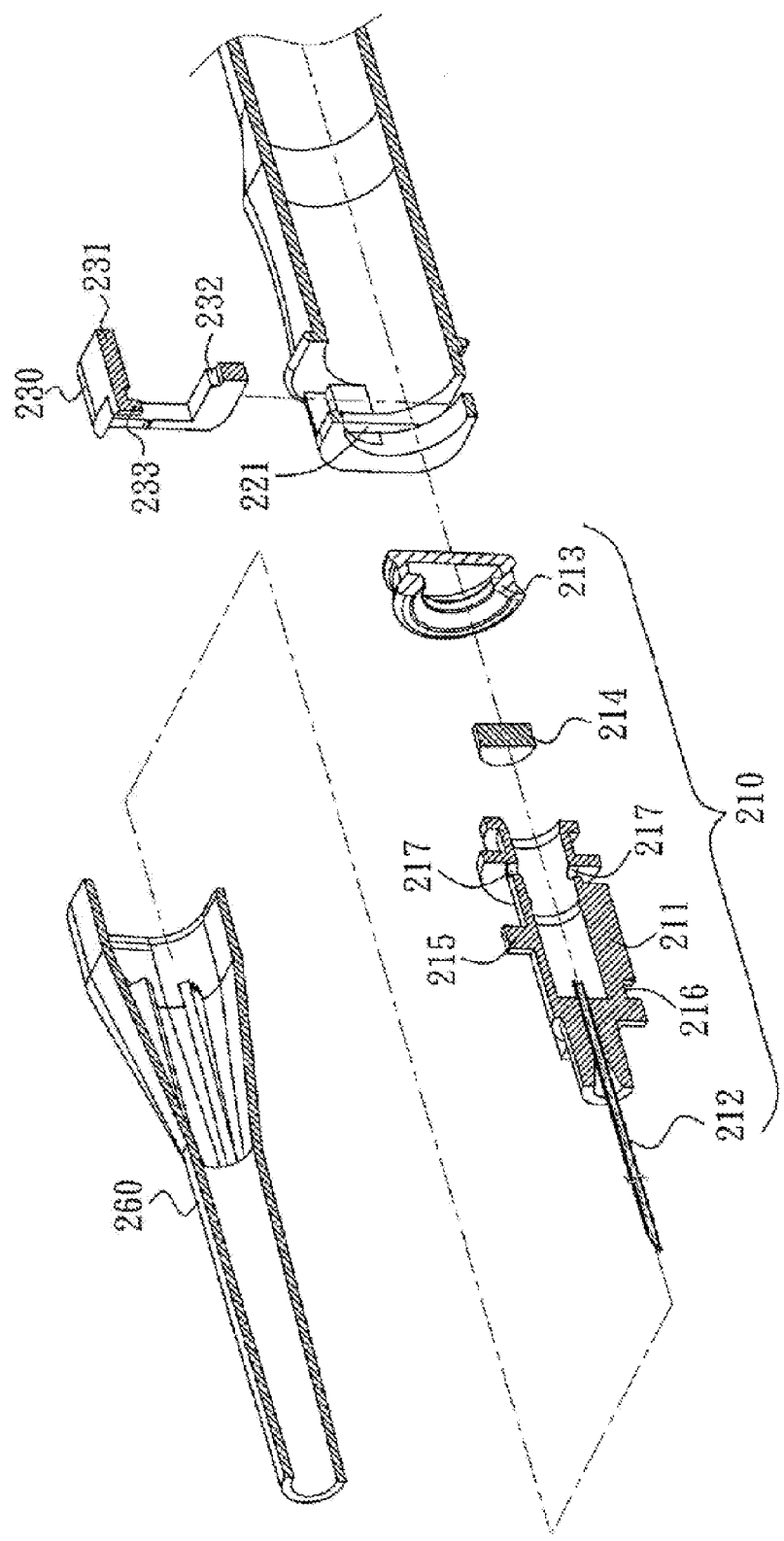
FIG. 1D is a partial enlarged view of the barrel, stopper and needle assembly.

Please refer to FIGS. 1A, 1B and 1D. The needle assembly 210 has a needle 212, a needle hub 211 and a needle piston 213. The needle 212 and the needle piston 213 are fastened onto a tip end and a root end of the needle hub 211, respectively. Preferably, the needle assembly 210 further includes a plug 214 received in the needle hub 211 and a vent 217 in the needle hub 211. The plug 214 corresponds to the vent 217 in position for controlling a direction and flow of the liquid flowing in the needle assembly 210. The catheter 250 is axially connected onto the needle hub 211 and passed through by the needle 212.

Please refer to FIGS. 1C and 1D. The vacuum generator 240 has a plunger 242 and a vacuum piston 241 mounted on an end thereof. The plunger 242 protrudes from an opening at the second end of the barrel 220. The vacuum piston 241 is made of a flexible material such as rubber and is formed into a cup shape. The vacuum piston 241 is slidably received in the barrel 220 and normally abuts against the needle piston 213 which is located at the first end of the barrel 220. The plunger 242 is formed with a head 2422 for engaging with the vacuum piston 241 and a breakable neck 2421 near the head 2422. The vacuum piston 241 moves with the plunger 242 and make an airtight effect in the barrel 220.

Furthermore, the needle hub 211 is formed with a first protrusion 215 and a slot 216. The stopper 230 is a hollow body with a sheet 231, a second protrusion 233 extending from the sheet 231 and a latch 232. The first end of the barrel 220 is formed with a guiding trough 221 for receiving the stopper 230.

When assembling, as shown in FIG. 1D, the vacuum generator 240 and the needle assembly 210 are first put into the barrel 220 through the first end thereof, and then move the needle assembly 210 to the second end of the barrel 220. Next, the stopper 230 is movably put in the guiding trough 221. Then, push the plunger 242 to move the needle assembly 210 toward the first end of the barrel 220, adjust the stopper 230 relative to the needle hub 211 to engage the slot 216 with the latch 232 when the first protrusion 215 is blocked by the sheet 231. Meanwhile, the stopper 230 engages with the needle hub 211 and prevents the needle hub 211 from moving. Finally, the catheter 250 is secured onto the needle assemble 210 to make the catheter 250 abuts against the second protrusion 233. At this time, the stopper 230 is limited by the catheter 250 and thus being unmovable.

Figure 2A:
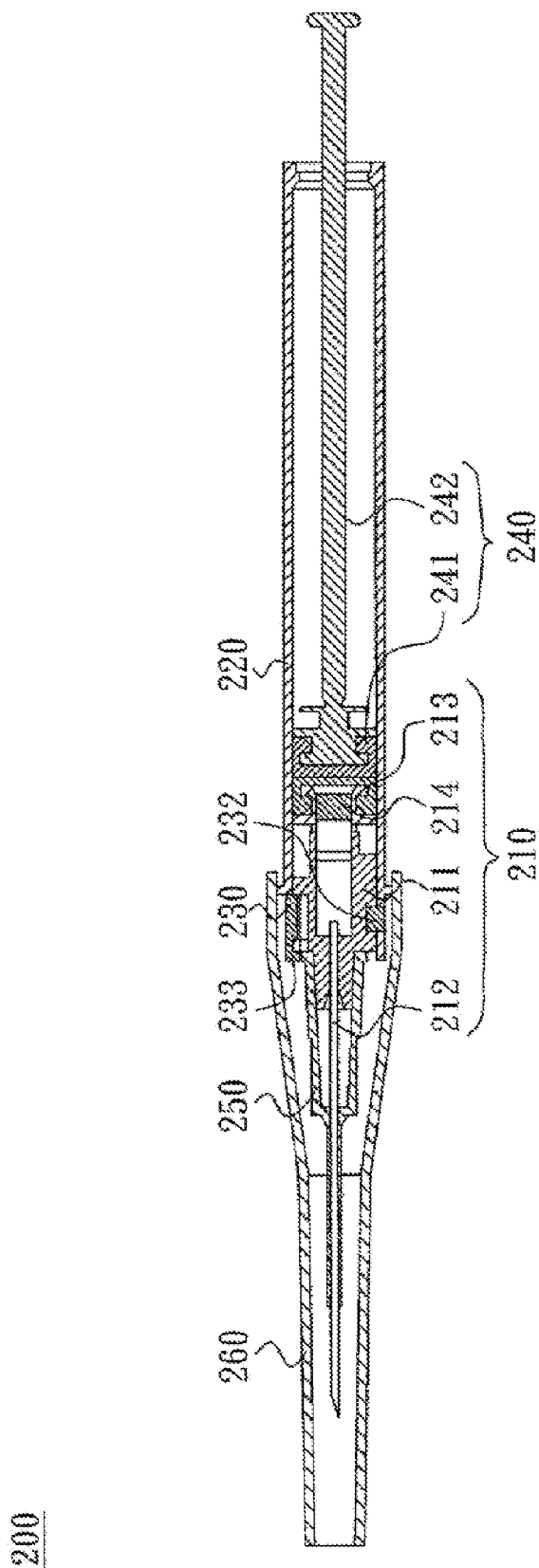
FIGS. 2A-2D depict using statuses of the invention.
Figure 2B:
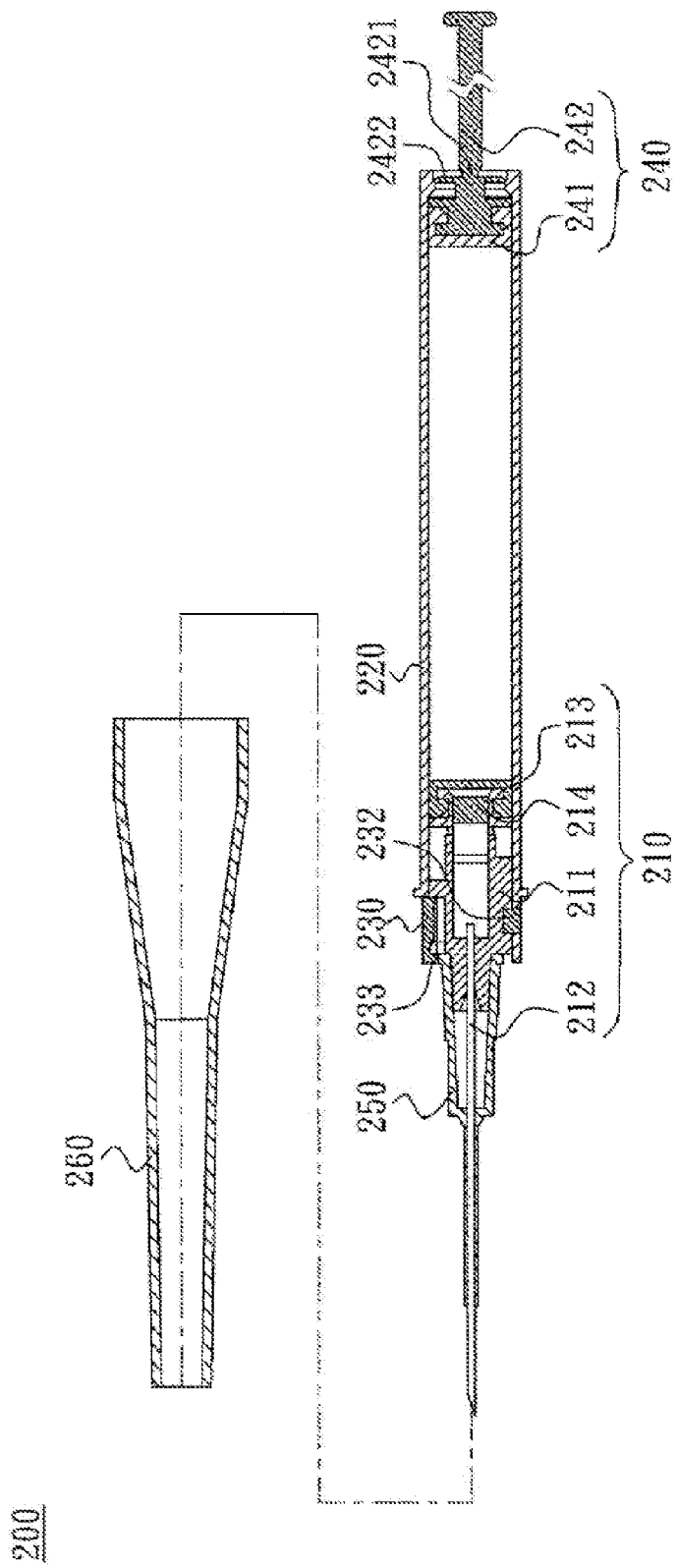

When using the catheter assembly 200 of the invention, as shown in the FIGS. 2A and 2B. The cap 260 is removed first, and then the plunger 242 with the vacuum piston 241 is pulled outward. At this time, the needle assembly 210 is stayed by the stopper 230 and a vacuum is formed within the barrel 220 between the vacuum piston 241 and the needle piston 213. The head 2422 is blocked by and seals up the second end of the barrel 220 as shown in FIG. 2B. As a result, outside air cannot flow back into the barrel 220 to keep the plunger 242 staying.

Figure 2C:
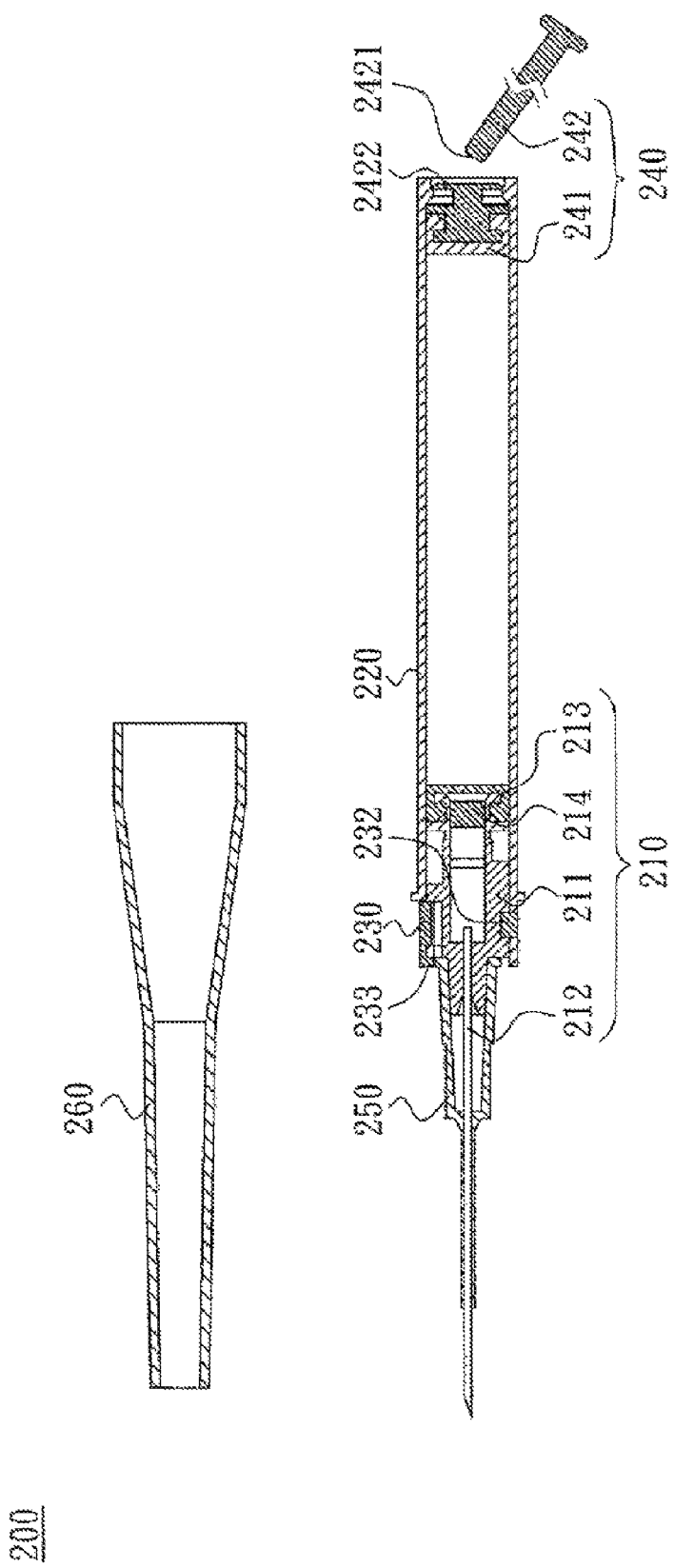

Referring to FIG. 2C, the plunger 242 can be broken at the breakable neck 2421. As abovementioned, the catheter 250 abuts against the second protrusion 233 and the stopper 230 is limited by the catheter 250 to be unmovable. After that, the intravenous catheter set 200 can be stabbed into a patient's skin with detaining the catheter 250 on the patient's skin and separating the catheter 250 from the needle assembly 210. Because the catheter 250 has escaped from the tip end of the needle hub 211, the stopper 230 is not blocked by the catheter 250 any longer and becomes moveable.

Figure 2D:
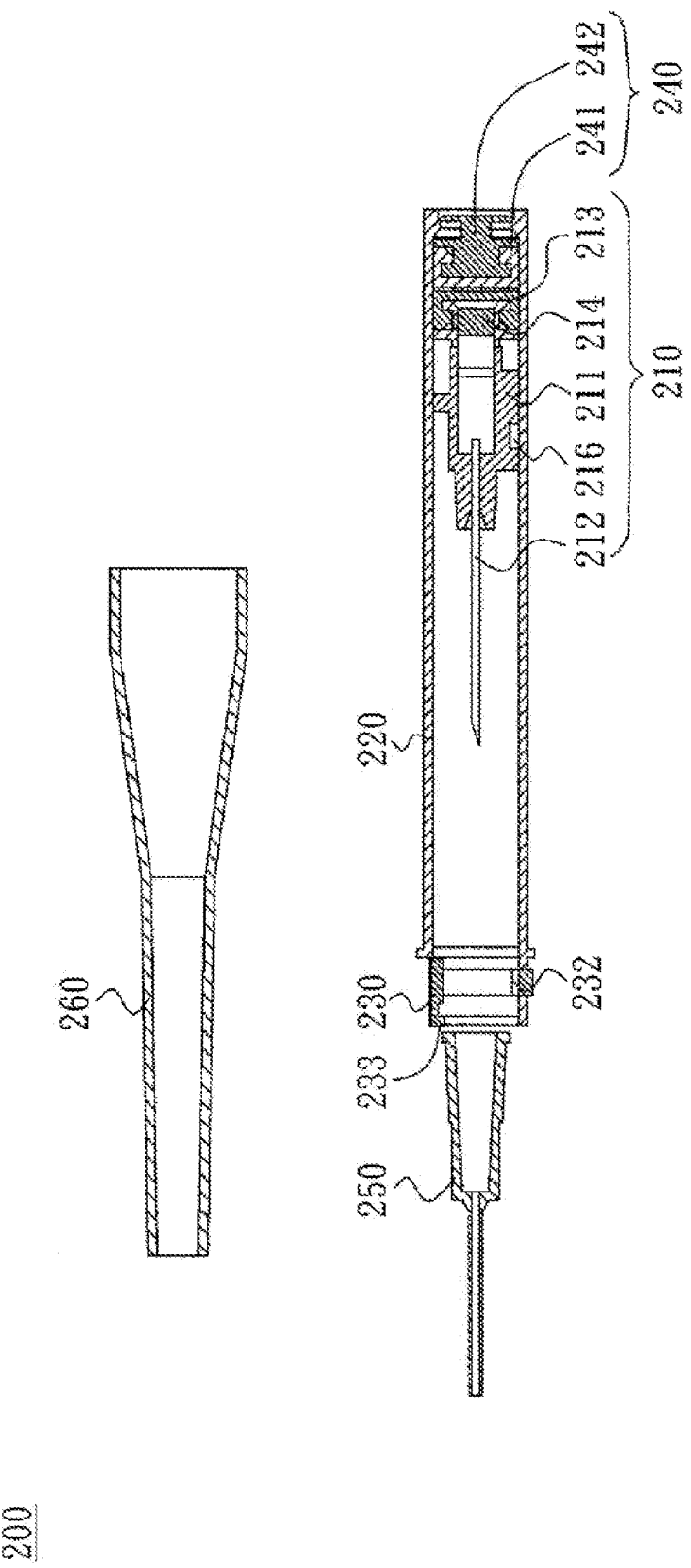

Please refer to FIG. 2D. When the stopper 230 is pressed down to move along the guiding trough 221, the slot 216 will not engage with the latch 232 any longer and the needle assembly 210 becomes moveable. At this time, the needle assembly 210 will be immediately pulled toward the second end of the barrel 220 by the suction from the vacuum in the barrel 220. As a result, the needle assembly 210 including the needle 212 is completely retracted and cloaked in the barrel 220.

While the forgoing is directed to preferred embodiments of the present invention, other and further embodiments of the invention may be devised without departing from the basic scope thereof. As such, the appropriate scope of the invention is to be determined according to the claims.

What is claimed is:

1. An intravenous catheter set comprising:
   a barrel having a first end and a second end;
   a needle assembly, disposed at the first end of the barrel, comprising a needle, a needle hub and a needle piston, wherein the needle is rooted on a tip end of the needle hub, and the needle piston is fastened onto a root end of the needle hub;
   a catheter, axially connected onto the tip end of the needle hub and passed through by the needle;
   a stopper, operably disposed at the first end of the barrel, and normally stopping the needle hub from moving; and
   a vacuum generator, axially disposed in the barrel, and comprising a plunger and a vacuum piston mounted on an end of the plunger, wherein the vacuum piston is slidably received in the barrel and normally abuts against the needle piston, and the plunger protrudes from the second end of the barrel;
   wherein the barrel forms a vacuum when the plunger is pulled outward, the needle assembly will be pulled toward the second end of the barrel by the vacuum and completely retracted in the barrel when the stopper releases the needle hub.

2. The intravenous catheter set of claim 1, further comprising a plug received in the needle hub.

3. The intravenous catheter set of claim 1, wherein the plunger further comprises a head for connecting the vacuum piston and sealing up the second end of the barrel.

4. The intravenous catheter set of claim 1, wherein the plunger is formed with a breakable neck.

5. The intravenous catheter set of claim 1, wherein the barrel is formed with a guiding trough for receiving the stopper.

6. The intravenous catheter set of claim 1, wherein the needle hub is formed with a first protrusion and a slot, and the stopper is a hollow body with a sheet, a second protrusion extending from the sheet and a latch.

7. The intravenous catheter set of claim 6, wherein the first protrusion is blocked by the sheet when the needle assembly is located at the first end of the barrel.

8. The intravenous catheter set of claim 6, wherein the slot engages with the latch when the needle assembly is located at the first end of the barrel.

9. The intravenous catheter set of claim 6, wherein the catheter abuts against the second protrusion when the needle assembly is located at the first end of the barrel.

* * * * *